United States Patent
Stock et al.

(10) Patent No.: US 11,365,168 B2
(45) Date of Patent: Jun. 21, 2022

(54) PREPARATION OF 5-ARYL-PENTANOLS

(71) Applicant: BASF SE, Ludwigshafen am Rhein (DE)

(72) Inventors: Christoph Stock, Ludwigshafen am Rhein (DE); Irene De Wispelaere, Antwerp (BE); Bernhard Brunner, Ludwigshafen am Rhein (DE); Wolfgang Krause, Lampertheim (DE); Ralf Pelzer, Lampertheim (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 17/421,311

(22) PCT Filed: Jan. 10, 2020

(86) PCT No.: PCT/EP2020/050490
§ 371 (c)(1),
(2) Date: Jul. 7, 2021

(87) PCT Pub. No.: WO2020/144307
PCT Pub. Date: Jul. 16, 2020

(65) Prior Publication Data
US 2022/0106243 A1 Apr. 7, 2022

(30) Foreign Application Priority Data

Jan. 11, 2019 (EP) .................................... 19151386

(51) Int. Cl.
*C07C 29/60* (2006.01)
(52) U.S. Cl.
CPC .................................. *C07C 29/60* (2013.01)

(58) Field of Classification Search
CPC ...................................................... C07C 29/60
See application file for complete search history.

(56) References Cited

U.S. PATENT DOCUMENTS

2003/0060667 A1   3/2003   Umada et al.

FOREIGN PATENT DOCUMENTS

CH    655932 A5    5/1986
EP    1298118 A2   4/2003

OTHER PUBLICATIONS

International Search Report and Written Opinion received for PCT Patent Application No. PCT/EP2020/050490, dated May 8, 2020, 9 pages (2 pages of English Translation and 7 pages of Original Document).
Li et al., "Asymmetric Hydrogenation of Allylic Alcohols Using Ir—N,P Complexes", ACS Catalysis, vol. 6, 2016, pp. 8342-8349.
Matteoli et al., "Asymmetric catalysis in fragrance chemistry: a new synthetic approach to enantiopure Phenoxanol (Registered) Citralis (Registered) and Citralis Nitrile (Registered)", Tetrahedron: Asymmetry, vol. 18, 2007, pp. 797-802.
Superchi et al., "Asymmetric Addition of Dimethylzinc to Alkylidenmalonates Mediated by Phosphorous Ligands: A New Synthetic Route to Floral Fragrances", Chirality, vol. 23, 2011, pp. 761-767.
Yadav et al., "Enzymatic kinetic resolution of racemic 4-tetrahydropyranols by Candida rugosa lipase", Tetrahedron Letters, vol. 48. No. 26, Jun. 25, 2007, pp. 4631-4633.

*Primary Examiner* — Sikarl A Witherspoon
(74) *Attorney, Agent, or Firm* — Faegre Drinker Biddle & Reath LLP

(57) ABSTRACT

The present invention relates to a method for preparing 5-aryl pentanols from 2-aryl-4-hydroxytetrahydropyrans as starting materials.

19 Claims, No Drawings

PREPARATION OF 5-ARYL-PENTANOLS

CROSS-REFERENCE TO RELATED APPLICATIONS

This application is a national stage application (under 35 U.S.C. § 371) of PCT/EP2020/050490, filed Jan. 10, 2020, which claims benefit of European Application No. 19151386.0, filed Jan. 11, 2019, both of which are incorporated herein by reference in their entirety.

BACKGROUND OF THE INVENTION

The present invention relates to a method for preparing 5-arylpentanols from 2-aryl-4-hydroxytetrahydropyrans as starting materials.

PRIOR ART

The increasing demand for fragrances having interesting scent notes does not necessarily require novel olfactory active molecules. A novel combination of known aroma substances and flavorings can also result in novel odor profiles. There is therefore an urgent need for new and simple ways to synthesize known aroma substances and flavorings.

5-Arylpentanols are widely used as aroma substances and flavorings. A known representative of this class is 3-methyl-5-phenylpentan-1-ol (Phenoxanol®), which has a floral scent note.

CH 655 932 describes a method for preparing 5-aryl-3-methylpentanol by hydrogenolysis of pyran derivatives of the formula

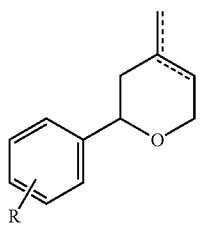

and especially of 2-phenyl-4-methylenepyran in the presence of a metal catalyst and an acidic substance such as a protic acid or an acidic diatomaceous earth.

US 2003/0060667 describes a method for preparing 3-methyl-5-phenylpentanol by hydrogenolysis of 6-phenyl-4-methyl-5,6-dihydro-2H-pyran in the presence of a supported palladium catalyst without additional use of an acidic substance.

U. Matteoli et al., Tetrahedron Asymmetry 2007, 18, 797 describes an enantioselective method for producing Phenoxanol® (3-methyl-5-phenylpentanol), Citralis® (3-methyl-5-phenylpentanal) and Citralis Nitrile® (3-methyl-5-phenylpentane-1-nitrile). The method is based on an asymmetric hydrogenation of (Z)- or (E)-3-methyl-5-phenylpent-2-en-1-ol in the presence of an iridium catalyst. Firstly, Phenoxanol is obtained, which is oxidized to Citralis. Citralis may be converted to Citralis Nitrile in a further reaction.

S. Superchi et al., Chirality 2011, 23, 761-767 describes a copper-catalyzed asymmetric addition reaction of dimethyl zinc to diethyl (3-phenylpropylidene)malonate for the production of Phenoxanol®. This reaction takes place in the presence of chiral phosphite ligands. The Phenoxanol® obtained may be converted to Citralis® and Citralis Nitrile® in a subsequent reaction.

P. G. Anderson et al., ACS Catalysis 2016, 6, 8342 describes the preparation of γ,γ-disubstituted and β,γ-disubstituted allyl alcohols. The allyl alcohols are hydrogenated in the presence of an iridium-based N,P catalyst, wherein the corresponding hydrogenation products are obtained.

There is still a great need for effective methods for preparing 5-arylpentanols from readily available starting materials.

The object of the present invention is to provide an improved method for preparing 5-arylpentanols.

Surprisingly, it has now been found that 5-arylpentanols, especially 3-methyl-5-phenylpentan-1-ol, can be obtained by a rapid route by hydrogenating 2-aryl-4-hydroxytetrahydropyrans in the presence of a hydrogenation catalyst under acidic conditions.

SUMMARY OF THE INVENTION

The invention relates to a method for preparing compounds of the general formula (I)

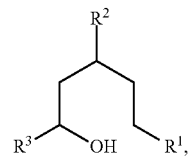

where
$R^1$ is selected from aryl having 6 to 20 carbon atoms that is unsubstituted or substituted by 1, 2, 3, 4 or 5 substituents selected from $C_1$-$C_{12}$-alkyl, $C_1$-$C_{12}$-alkoxy, phenyl and benzyl;
$R^2$ is selected from hydrogen and $C_1$-$C_6$-alkyl;
$R^3$ is selected from hydrogen and $C_1$-$C_6$-alkyl;
comprising the steps of:
a) providing at least one compound of the general formula (II)

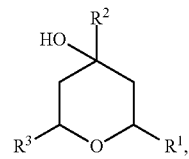

where $R^1$, $R^2$ and $R^3$ have the definitions specified above,
b) hydrogenation of the compound (II) in the presence of a hydrogenation catalyst under acidic conditions.

DESCRIPTION OF THE INVENTION

The process according to the invention has the following advantages:
using the reaction provided according to the invention, access to 5-arylpentanols and especially to 3-methyl-5-phenylpentan-1-ol (Phenoxanol®) is made possible which only requires one reaction stage (one-pot synthesis).

the 3-methyl-5-phenylpentan-1-ol (Phenoxanol®) produced can be used as starting material for the production of Citralis® and Citralis Nitrile®.

no further expensive and/or potentially hazardous reagents have to be used to produce the 5-arylpentanols and especially 3-methyl-5-phenylpentan-1-ol.

Unless specified more precisely below, the invention comprises all possible isomers, i.e. all possible enantiomers and diastereomers, all enantiomers in pure form and also racemic and optically active mixtures of the enantiomers of these compounds.

In the context of the present invention, the expression straight-chain or branched alkyl preferably represents $C_1$-$C_6$-alkyl and particularly preferably $C_1$-$C_4$-alkyl. In particular, alkyl is methyl, ethyl, n-propyl, isopropyl, n-butyl, isobutyl (2-methylpropyl), sec-butyl (1-methylpropyl), tert-butyl (1,1-dimethylethyl), n-pentyl or n-hexyl. Alkyl is especially methyl, ethyl, n-propyl, isopropyl, or isobutyl.

In the context of the present invention, the expression straight-chain or branched alkoxy preferably represents $C_1$-$C_6$-alkoxy and particularly preferably $C_1$-$C_4$-alkoxy. In particular, alkoxy is methoxy, ethoxy, n-propyloxy, isopropyloxy, n-butyloxy, isobutyloxy, sec-butyloxy, tert-butyloxy, n-pentyloxy or n-hexyloxy. Alkoxy is especially methoxy, ethoxy, n-propyloxy, isopropyloxy, or isobutyloxy.

In the context of the present invention, the expression "aryl" comprises mono- or poly-cyclic aromatic hydrocarbon radicals typically having 6 to 20, preferably 6 to 14, particularly preferably 6 to 10 carbon atoms. Examples of aryl are particularly phenyl, naphthyl, indenyl, fluorenyl, anthracenyl, phenanthrenyl, naphthacenyl, chrysenyl, pyrenyl, etc., and especially phenyl or naphthyl.

Substituted aryls may have one or more substituents (e.g. 1, 2, 3, 4 or 5) depending on the number and size of their ring systems. These are each preferably independently selected from $C_1$-$C_6$-alkyl and $C_1$-$C_6$-alkoxy. Examples of substituted aryl radicals are 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl, 2,4,6-tri-tert-butylphenyl, 1-methyl-2-naphthyl, 3-methyl-2-naphthyl, 1,3-dimethyl-2-naphthyl, 5,6,7,8-tetramethyl-2-naphthyl, 5-methyl-2-naphthyl, 6-methyl-2-naphthyl, 7-methyl-2-naphthyl, 8-methyl-2-naphthyl.

$R^1$ in the compounds of the formula (I) and (II) is preferably phenyl that is unsubstituted or substituted by 1, 2, 3, 4 or 5 substituents selected from $C_1$-$C_6$-alkyl, and $C_1$-$C_6$-alkoxy.

$R^1$ in the compounds of the formula (I) and (II) is particularly preferably phenyl, 2-, 3- or 4-methylphenyl, 2,4-, 2,5-, 3,5- or 2,6-dimethylphenyl, 2,4,6-trimethylphenyl, 2-, 3- or 4-ethylphenyl, 2,4-, 2,5-, 3,5- or 2,6-diethylphenyl, 2,4,6-triethylphenyl, 2-, 3- or 4-propylphenyl, 2,4-, 2,5-, 3,5- or 2,6-dipropylphenyl, 2,4,6-tripropylphenyl, 2-, 3- or 4-isopropylphenyl, 2,4-, 2,5-, 3,5- or 2,6-diisopropylphenyl, 2,4,6-triisopropylphenyl, 2-, 3- or 4-butylphenyl, 2,4-, 2,5-, 3,5- or 2,6-dibutylphenyl, 2,4,6-tributylphenyl, 2-, 3- or 4-isobutylphenyl, 2,4-, 2,5-, 3,5- or 2,6-diisobutylphenyl, 2,4,6-triisobutylphenyl, 2-, 3- or 4-sec-butylphenyl, 2,4-, 2,5-, 3,5- or 2,6-di-sec-butylphenyl, 2,4,6-tri-sec-butylphenyl, 2-, 3- or 4-tert-butylphenyl, 2,4-, 2,5-, 3,5- or 2,6-di-tert-butylphenyl or 2,4,6-tri-tert-butylphenyl.

In a specific embodiment, $R^1$ in the compounds of the formula (I) and (II) is phenyl.

$R^2$ in the compounds of the formula (I) and (II) is preferably hydrogen and $C_1$-$C_4$-alkyl.

Preferred definitions in accordance with the invention for the radical $R^2$ in the compounds of the formula (I) and (II) are therefore, for example hydrogen, methyl, ethyl, n-propyl, isopropyl, n-butyl, isobutyl, preferably methyl, ethyl, n-propyl, isopropyl, n-butyl and isobutyl.

In a specific embodiment, $R^2$ in the compounds of the formula (I) and (II) is methyl.

$R^3$ in the compounds of the formula (I) and (II) is preferably hydrogen and $C_1$-$C_4$-alkyl.

Preferred definitions in accordance with the invention for the radical $R^3$ in the compounds of the formula (I) and (II) are therefore, for example hydrogen, methyl, ethyl, n-propyl, isopropyl, n-butyl, isobutyl, preferably methyl, ethyl, n-propyl, isopropyl, n-butyl and isobutyl.

In a specific embodiment, $R^3$ in the compounds of the formula (I) and (II) is hydrogen.

The present invention therefore relates in a preferred embodiment to a method for preparing and isolating 3-methyl-5-phenylpentan-1-ol (Phenoxanol®) of the formula (Ia)

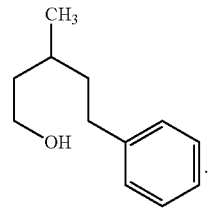

(I.a)

Step a)

Suitable starting materials for use in step a) may be at least one compound of the general formula (II)

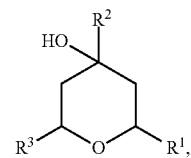

where $R^1$ is selected from aryl having 6 to 20 carbon atoms that is unsubstituted or substituted by 1, 2, 3, 4 or 5 substituents selected from $C_1$-$C_{12}$-alkyl, $C_1$-$C_{12}$-alkoxy, phenyl and benzyl;

$R^2$ is selected from hydrogen and $C_1$-$C_6$-alkyl;

$R^3$ is selected from hydrogen and $C_1$-$C_6$-alkyl.

$R^1$ is preferably phenyl that is unsubstituted or substituted by 1, 2, 3, 4 or 5 substituents selected from $C_1$-$C_6$-alkyl, and $C_1$-$C_6$-alkoxy.

$R^1$ is particularly preferably phenyl, 2-, 3- or 4-methylphenyl, 2,4-, 2,5-, 3,5- or 2,6-dimethylphenyl, 2,4,6-trimethylphenyl, 2-, 3- or 4-ethylphenyl, 2,4-, 2,5-, 3,5- or 2,6-diethylphenyl, 2,4,6-triethylphenyl, 2-, 3- or 4-propylphenyl, 2,4-, 2,5-, 3,5- or 2,6-dipropylphenyl, 2,4,6-tripropylphenyl, 2-, 3- or 4-isopropylphenyl, 2,4-, 2,5-, 3,5- or 2,6-diisopropylphenyl, 2,4,6-triisopropylphenyl, 2-, 3- or 4-butylphenyl, 2,4-, 2,5-, 3,5- or 2,6-dibutylphenyl, 2,4,6-tributylphenyl, 2-, 3- or 4-isobutylphenyl, 2,4-, 2,5-, 3,5- or 2,6-diisobutylphenyl, 2,4,6-triisobutylphenyl, 2-, 3- or 4-sec-butylphenyl, 2,4-, 2,5-, 3,5- or 2,6-di-sec-butylphenyl, 2,4,6-tri-sec-butylphenyl, 2-, 3- or 4-tert-butylphenyl, 2,4-, 2,5-, 3,5- or 2,6-di-tert-butylphenyl or 2,4,6-tri-tert-butylphenyl.

In a specific embodiment, $R^1$ is phenyl.

$R^2$ is preferably hydrogen and $C_1$-$C_4$-alkyl.

Preferred definitions in accordance with the invention for the radical $R^2$ in the compounds of the formula (I) and (II) are therefore, for example hydrogen, methyl, ethyl, n-propyl, isopropyl, n-butyl, isobutyl, preferably methyl, ethyl, n-propyl, isopropyl, n-butyl and isobutyl.

In a specific embodiment, $R^2$ is methyl.

$R^3$ is preferably hydrogen and $C_1$-$C_4$-alkyl.

Preferred definitions in accordance with the invention for the radical $R^3$ in the compounds of the formula (I) and (II) are therefore, for example hydrogen, methyl, ethyl, n-propyl, isopropyl, n-butyl, isobutyl, preferably methyl, ethyl, n-propyl, isopropyl, n-butyl and isobutyl.

In a specific embodiment, $R^3$ is hydrogen.

The synthetic route for the preparation of the compound of the formula (II) is described in WO 2010/133473, WO 2015/158454 and WO 2014/060345.

Step b)

In accordance with the invention, the compound of the formula (II) is subjected to an elimination followed by hydrogenation in the presence of a hydrogenation catalyst under acidic conditions. By means of the elimination and hydrogenation in step b), the compound of the formula (II) is converted to the corresponding compound of the formula (I).

The elimination followed by hydrogenation is preferably carried out in one reaction stage (one-pot synthesis), i.e. without isolation of intermediate compounds.

In the context of the invention, the expression "under acidic conditions" is understood to mean that the reaction takes place in the presence of an acid. Acid is understood to mean any substance which has Brönsted or Lewis acidity.

Such substances are preferably selected from proton donors, electron acceptors and mixtures thereof.

Proton donors are preferably selected from molecular protic acids, ion exchangers and mixtures thereof.

Electron acceptors are preferably selected from acidic molecular element compounds, oxidic acidic solids and mixtures thereof.

Suitable molecular protic acids are, for example, hydrochloric acid, sulfuric acid, phosphoric acid, nitric acid, acetic acid, formic acid, trifluoromethylsulfonic acid, methanesulfonic acid, p-toluenesulfonic acid and mixtures thereof.

Suitable acidic molecular element compounds are, for example, aluminum chloride, boron trifluoride, zinc chloride, phosphorus pentafluoride, arsenic trifluoride, tin tetrachloride, titanium tetrachloride, antimony pentafluoride and mixtures thereof.

Suitable oxidic acidic solids are, for example, zeolites, silicates, aluminates, aluminosilicates, clays and mixtures thereof.

Suitable ion exchangers are acidic cationic ion exchangers.

In the context of the present invention, the expression "acidic cation exchanger" is understood to mean those cation exchangers in the $H^+$ form having acidic groups, usually sulfonic acid groups, the matrix of which can be gel-like or macroporous. A preferred embodiment of the method according to the invention is accordingly characterized in that an acidic cation exchanger containing or comprising sulfonic acid groups is used.

Acidic cation exchangers are, in particular, ion exchange resins in the $H^+$ form. Useful examples of these include:

acidic ion exchangers (such as Amberlyst, Amberlite, Dowex, Lewatit, Purolite, Serdolit), which are based on polystyrene and which comprise copolymers of styrene and divinylbenzene as a support matrix, having sulfonic acid groups in $H^+$ form, ion exchange groups functionalized with sulfonic acid groups ($-SO_3H$).

The ion exchangers differ in the structure of their polymer skeletons and a distinction is made between gel-like and macroporous resins. The acidic ion exchange resins are generally regenerated using hydrochloric acid and/or sulfuric acid.

Nafion® is the Dupont company name for perfluorinated polymeric ion exchange resins. These are perfluorinated ion exchange materials, consisting of fluorocarbon-based chains and perfluorinated side chains comprising sulfonic acid groups. The resins are produced by copolymerization of perfluorinated, terminally unsaturated and sulfonyl fluoride-functionalized ethoxylates with perfluoroethene. Nafion® is one of the gel-like ion exchange resins. An example of such a perfluorinated polymeric ion exchange resin includes Nafion®>NR-50.

The acidic cation exchangers are generally used in the $H^+$ form, in which the ion exchanger comprises a polymer skeleton containing sulfonic acid groups and either being in gel form or comprising macroporous resins.

A very particularly preferred embodiment of the method according to the invention is characterized in that the ion exchanger is based on a polystyrene skeleton having sulfonic acid groups or on a perfluorinated ion exchange resin having sulfonic acid groups.

The commercially available acidic cation exchangers are known under the trade names Lewatit® (Lanxess), Purolite® (The Purolite Company), Dowex® (Dow Chemical Company), Amberlite® (Rohm and Haas Company), Amberlyst™ (Rohm and Haas Company). In accordance with the invention, preferred acidic cation exchangers include, for example: Lewatit® K 1221, Lewatit® K 1461, Lewatit® K 2431, Lewatit® K 2620, Lewatit® K 2621, Lewatit® K 2629, Lewatit® K 2649, Amberlite® IR 120, Amberlyst®131, Amberlyst®15, Amberlyst® 31, Amberlyst® 35, Amberlyst® 36, Amberlyst® 39, Amberlyst® 46, Amberlyst® 70, Purolite® SGC650, Purolite® C100H, Purolite® C150H, Dowex® 50X8, Dowex® 88, Serdolit® red and Nation® NR-50.

In the context of a preferred embodiment, the reaction of compound (II) to be carried out in accordance with the invention is carried out in the presence of at least one acidic cation exchanger selected from the group of cation exchangers comprising Lewatit® K 1221, Lewatit® K 2629, Amberlyst® 131, Amberlyst® 35 Purolite® SGC650, Purolite® C100H, Purolite® C15OH, Amberlite® IR 120, Dowex® 88 and Dowex® 50X8.

Particularly preferred acidic cation exchangers according to the invention are the acidic cation exchangers Amberlyst® 35, Dowex® 88 and/or Amberlite® IR 120.

An acidic cation exchanger which is very particularly preferred according to the invention is Amberlyst® 35 which, like the other cation exchangers mentioned, is commercially available.

The acidic ion exchange resins are generally regenerated using hydrochloric acid and/or sulfuric acid.

The hydrogenation in step b) may be carried out in a conventional manner using a hydrogenation catalyst of the prior art. The hydrogenation may be carried out catalytically either in the gas phase or in the liquid phase. The hydrogenation in step b) is preferably carried out in the liquid phase in the presence of a heterogeneous hydrogenation catalyst and a hydrogen-containing gas.

Suitable hydrogenation catalysts include, in principle, all homogeneous and heterogeneous catalysts suitable for hydrogenating unsaturated organic compounds. These include, for example, metals, metal oxides, various metal compounds thereof or mixtures thereof. Suitable hydrogenation catalysts preferably comprise at least one transition metal, preferably from the transition groups I and VI to VIII of the Periodic Table of the Elements. These preferably include Pd, Pt, Ni, Rh, Ru, Co, Fe, Zn, Cu, Re or mixtures thereof.

The hydrogenation catalyst may comprise at least one further metal/element which is different from the metals described above. The further metal/element is preferably selected from alkali metals, alkaline earth metals, aluminum, silicon, lanthanoids and mixtures thereof.

The proportion of the further metal/element is preferably in the range from 0.1 to 10% by weight, based on the total weight of the active part of the hydrogenation catalyst (excluding the carrier).

The catalysts may consist solely of the active components, or the active components may be applied to supports. Suitable carrier materials are, e.g. zirconium dioxide, barium oxide, zinc oxide, magnesium oxide, titanium oxide, aluminum oxide, $TiO_2$—$Al_2O_3$, $ZrO_2$—$Al_2O_3$, zeolites, hydrotalcite, silicon carbide, tungsten carbide, silicon dioxide, carbon, especially activated carbon or sulfated carbon, diatomaceous earth, clay, barium sulfate, calcium carbonate and mixtures.

In one embodiment, the support materials at the same time comprise an acid used according to the invention or consist thereof.

To increase the catalytic activity, Ni, Cu or Co, also in the form of Raney catalysts, Pd, Pt, Rh, Ru, Co, Fe, Zn, Cu, or mixtures thereof, can be used as a metal sponge having a very large surface area.

Advantageously, palladium on carbon, palladium on $Al_2O_3$, palladium on $SiO_2$ or platinum on carbon is preferably used for the hydrogenation in step b) of the method according to the invention. Palladium on carbon is particularly preferably used advantageously.

Other suitable catalysts comprise, for example, 80 to 100% by weight nickel and/or cobalt and up to 20% by weight activating metals such as copper and/or chromium. Such catalysts are particularly advantageously used as supported catalysts.

The content of catalytically active metals in such supported catalysts, the support material being carbon, is generally from 0.05 to 10% by weight, based on the sum of catalytically active metals and support.

The content of catalytically active metals in such supported catalysts, where the support material is an oxide, e.g. $Al_2O_3$ or $SiO_2$, is generally 0.01 to 1% by weight, based on the sum of catalytically active metals and support.

The catalysts for the hydrogenation in step b) may be used as shaped bodies. Examples comprise catalyst extrudates such as ribbed extrudates and other extrudate forms, eggshell catalysts, tablets, rings, spheres, spall, etc.

The hydrogenation in step b) is preferably carried out at a temperature of 60 to 200° C., preferably 120 to 150° C.

If the reaction is carried out in the gas phase, the pressure is preferably within a range from 0.9 to 50 bar, particularly preferably 1 to 20 bar.

If the reaction is carried out in the liquid phase, the pressure is preferably within a range from 0.9 to 200 bar, particularly from 40 to 80 bar.

The hydrogenation in step b) can be carried out in one reactor or in a plurality of reactors connected in series. The hydrogenation can be effected continuously or batchwise. For the batchwise hydrogenation a pressure vessel, for example, may be used. Suitable pressure vessels are, for example, autoclaves equipped with an apparatus for heating and for stirring the reactor contents. The hydrogenation is preferably carried out in the liquid phase over a fixed bed, preferably in liquid phase mode or trickle mode or in the form of a suspension catalysis. In this case, the catalysts are preferably used in the form of shaped bodies, for example in the form of pressed cylinders, tablets, pellets, wagonwheels, rings, stars, or extrudates such as solid extrudates, polylobal extrudates, hollow extrudates, honeycombs etc.

In suspension mode, heterogeneous catalysts are likewise used. The heterogeneous catalysts are usually used in a finely divided state and are in fine suspension in the reaction medium.

In the case of hydrogenation over a fixed bed, a reactor with a fixed bed arranged in the interior thereof, through which the reaction medium flows, is used. The fixed bed may be formed from a single bed or from a plurality of beds. Each bed may have one or more zones, at least one of the zones comprising a material active as a hydrogenation catalyst. Each zone may have one or more different catalytically active materials and/or one or more different inert materials. Different zones may each have identical or different compositions. It is also possible to provide a plurality of catalytically active zones separated from one another, for example, by inert beds. The individual zones may also have different catalytic activity. To this end, it is possible to use different catalytically active materials and/or to add an inert material to at least one of the zones. The reaction medium which flows through the fixed bed comprises at least one liquid phase in accordance with the invention. The reaction medium may also additionally comprise a gaseous phase.

The reactors used in the hydrogenation in suspension are especially loop apparatuses such as jet loops or propeller loops, stirred tanks, which may also be configured as stirred tank cascades, bubble columns or airlift reactors.

The hydrogenation in step b) is preferably carried out in suspension mode.

The hydrogenation can be carried out with or without addition of a solvent. Useful solvents include alcohols, ethers, hydrocarbons such as methanol, ethanol, isopropanol, dioxane, tetrahydrofuran, n-pentane, hexane, cyclohexane, toluene, etc.

In one embodiment, the hydrogenation in step b) is carried out without addition of a solvent.

In another embodiment, the hydrogenation in step b) is carried out with addition of a solvent.

For the hydrogenation in step b), the compound of the formula (II) obtained in step a) can be brought into contact with a hydrogen-containing gas and a hydrogenation catalyst. Suitable hydrogen-containing gases are selected from hydrogen and mixtures of hydrogen with at least one inert gas. Suitable inert gases are, for example, nitrogen or argon. For the hydrogenation in step b), hydrogen is preferably used in undiluted form, typically at a purity of about 99.9% by volume.

The hydrogenation in step b) converts the compounds of the formula (II) to 5-arylpentanols (I). The starting material used for the hydrogenation preferably comprises compounds of the formula (II), where the radicals $R^1$, $R^2$ and $R^3$ have the definitions and preferences stated above. In a preferred embodiment, $R^1$ is preferably phenyl, $R^2$ is methyl and $R^3$ is hydrogen.

In a specific embodiment, the compounds (II) are converted to the compound of the formula (Ia), 3-methyl-5-phenylpentan-1-ol, by the hydrogenation in step b).

The compound of the formula (I) obtained in step b) can be converted to a form suitable for commercial use by simple purification steps.

If desired, the compound of the formula (I) obtained in step b) can be subjected to further processing. For this purpose, the compound (I) obtained in step b) can in principle be subjected to customary purification processes known to those skilled in the art. This includes, for example, filtration, neutralization, distillation, extraction or a combination thereof.

A fraction enriched in 5-arylpentanols (I) and a fraction depleted in 5-aryl pentanols (I) are preferably isolated from the hydrogenation product obtained in step b).

The compound (I) obtained in step b) is preferably subjected to a separation by distillation. Suitable apparatuses for distillative separation comprise distillation columns such as tray columns, which may be equipped with bubble-caps, sieve plates, sieve trays, structured packings, random packings, valves, side draws, etc., evaporators such as thin film evaporators, falling film evaporators, forced circulation evaporators, Sambay evaporators etc. and combinations thereof.

The compound (I) obtained in step b) is preferably subjected in step c) to a separation by distillation in at least one distillation column which is provided with separating internals.

To remove further water-soluble impurities, the fraction obtained in step c) enriched in 5-aryl pentanols (I) may be subjected to at least one washing step with water. Alternatively or additionally, the fraction obtained in step c) enriched in 5-aryl pentanols (I) may be subjected to a further purification by distillation.

The examples that follow serve to elucidate the invention without restricting it in any way.

EXAMPLES

Gas chromatographic analyses were carried out in accordance with the following method:
Column: ZB5 30 m×0.25 mm;
FD 1 μm;
Injector temperature: 200° C.; detector temperature 280° C.;
Temperature program: Starting temp.: 40° C., hold for 5 min, at 10° C./min to 300° C., 14 Min isothermal;
Retention times: 2-phenyl-4-hydroxy-4-methyltetrahydropyran (isomers): 27.41 min; 27.68 min
3-methyl-5-phenylpentanol: 26.41 min
Concentrations of the resulting crude products (% by weight) were determined by GC analysis using an internal standard.

Preparation of 3-methyl-5-phenylpentan-1-ol starting from 2-phenyl-4-hydroxy-4-methyltetrahydropyran in methanol

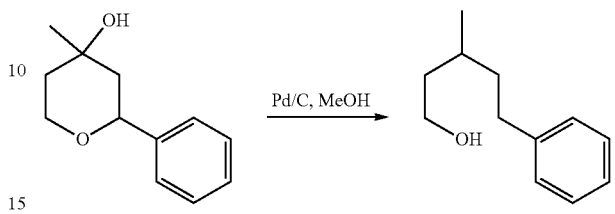

Example 1

6 g of 2-phenyl-4-hydroxy-4-methyltetrahydropyran, 60 g of methanol, 0.2 g of catalyst (5% Pd on carbon) and 0.2 g of the acidic ion exchanger Amberlyst 35 are weighed into an autoclave. This is sealed and incorporated into the autoclave station. The autoclave is then flushed once with nitrogen and once with hydrogen. Then 30 bar hydrogen are injected. After heating to 120° C., hydrogen is injected to 50 bar. The reaction mixture is stirred for 6 hours under these conditions. At full conversion of the reactant, 65.8% of product is found.

Example 2

6 g of 2-phenyl-4-hydroxy-4-methyltetrahydropyran, 20 g of methanol, 0.1 g of catalyst (10% Pd on carbon) and 0.2 g of the acidic ion exchanger Amberlyst 35 are weighed into an autoclave. This is sealed and incorporated into the autoclave station. The autoclave is then flushed once with nitrogen and once with hydrogen. Then 30 bar hydrogen are injected. After heating to 140° C., hydrogen is injected to 50 bar. The reaction mixture is stirred for 6 hours under these conditions. At full conversion of the reactant, 31% of product is found.

The invention claimed is:
1. A method for preparing compounds of the general formula (I)

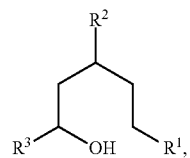

wherein
$R^1$ is selected from aryl having 6 to 20 carbon atoms that is unsubstituted or substituted by 1, 2, 3, 4 or 5 substituents selected from $C_1$-$C_{12}$-alkyl, $C_1$-$C_{12}$-alkoxy, phenyl and benzyl;
$R^2$ is selected from hydrogen and $C_1$-$C_6$-alkyl;
$R^3$ is selected from hydrogen and $C_1$-$C_6$-alkyl;
comprising the steps of:
a) providing at least one compound of the general formula (II)

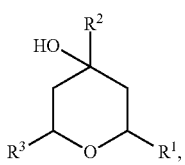

where $R^1$, $R^2$ and $R^3$ have the definitions specified above, b) hydrogenation of the compound (II) in the presence of a hydrogenation catalyst under acidic conditions.

2. The method according to claim 1, wherein $R^1$ is phenyl that is unsubstituted or substituted by 1, 2, 3, 4 or 5 substituents selected from $C_1$-$C_6$-alkyl, $C_1$-$C_6$-alkoxy.

3. The method according to claim 1, wherein $R^1$ is phenyl, 2-, 3- or 4-methylphenyl, 2,4-, 2,5-, 3,5- or 2,6-dimethylphenyl, 2,4,6-trimethylphenyl, 2-, 3- or 4-ethylphenyl, 2,4-, 2,5-, 3,5- or 2,6-diethylphenyl, 2,4,6-triethylphenyl, 2-, 3- or 4-propylphenyl, 2,4-, 2,5-, 3,5- or 2,6-dipropylphenyl, 2,4,6-tripropylphenyl, 2-, 3- or 4-isopropylphenyl, 2,4-, 2,5-, 3,5- or 2,6-diisopropylphenyl, 2,4,6-triisopropylphenyl, 2-, 3- or 4-butylphenyl, 2,4-, 2,5-, 3,5- or 2,6-dibutylphenyl, 2,4,6-tributylphenyl, 2-, 3- or 4-isobutylphenyl, 2,4-, 2,5-, 3,5- or 2,6-diisobutylphenyl, 2,4,6-triisobutylphenyl, 2-, 3- or 4-sec-butylphenyl, 2,4-, 2,5-, 3,5- or 2,6-di-sec-butylphenyl, 2,4,6-tri-sec-butylphenyl, 2-, 3- or 4-tert-butylphenyl, 2,4-, 2,5-, 3,5- or 2,6-di-tert-butylphenyl or 2,4,6-tri-tert-butylphenyl.

4. The method according to claim 1, wherein $R^2$ is selected from hydrogen and $C_1$-$C_4$-alkyl.

5. The method according to claim 1, wherein $R^3$ is selected from hydrogen and $C_1$-$C_4$-alkyl.

6. The method according to claim 1, wherein the hydrogenation in step b) is carried out in the presence of an acid selected from at least one protic acid, at least one Lewis acid, at least one acidic ion exchanger, at least one oxidic acidic solid, at least one acidic molecular element compound and mixtures thereof.

7. The method according to claim 1, wherein the hydrogenation in step b) is carried out in the presence of an acid which is selected from hydrochloric acid, sulfuric acid, phosphoric acid, nitric acid, acetic acid, formic acid, trifluoromethylsulfonic acid, methanesulfonic acid, p-toluenesulfonic acid, aluminum chloride, boron trifluoride, zinc chloride, phosphorus pentafluoride, arsenic trifluoride, tin tetrachloride, titanium tetrachloride, antimony pentafluoride and mixtures thereof.

8. The method according to claim 1, wherein the hydrogenation in step b) is carried out in the presence of an acidic cation exchanger.

9. The method according to claim 1, wherein the hydrogenation in step b) is carried out in the presence of an oxidic acidic solid which is selected from zeolites, silicates, aluminates, aluminosilicates and clays.

10. The method according to claim 1, wherein the catalyst comprises at least one transition metal selected from Pd, Pt, Ni, Rh, Ru, Co, Fe, Zn, Cu, Re or mixtures thereof.

11. The method according to claim 1, wherein the hydrogenation catalyst is a supported catalyst.

12. The method according to claim 1, wherein the catalyst support is selected from zirconium dioxide, zinc oxide, magnesium oxide, titanium oxide, aluminum oxide, barium oxide, $TiO_2$—$Al_2O_3$, $ZrO_2$—$Al_2O_3$, zeolites, hydrotalcite, silicon carbide, tungsten carbide, silicon dioxide, carbon, especially activated carbon or sulfated carbon, diatomaceous earth, clay, barium sulfate, calcium carbonate and mixtures thereof.

13. The method according to claim 1, wherein the temperature in step b) is in the range from 60 to 200° C.

14. The method according to claim 1, wherein the pressure in step b) is in a range from 900 mbar to 200 bar.

15. The method according to claim 1, wherein the method is carried out as a one-pot synthesis.

16. The method according to claim 1, wherein the temperature in step b) is in the range from 120 to 150° C., and the pressure in step b) is in a range from 40 to 80 bar.

17. The method according to claim 1, wherein $R^1$ is phenyl.

18. The method according to claim 1, wherein $R^2$ is methyl.

19. The method according to claim 1, wherein $R^3$ is hydrogen.

* * * * *